(12) United States Patent
Lopaschuk et al.

(10) Patent No.: US 7,432,247 B2
(45) Date of Patent: *Oct. 7, 2008

(54) METHODS OF CARDIOPROTECTION USING DICHLOROACETATE IN COMBINATION WITH AN INOTROPE

(75) Inventors: Gary D. Lopaschuk, Edmonton (CA); Ruth Collins-Nakai, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 770 days.

This patent is subject to a terminal disclaimer.

(21) Appl. No.: 10/778,791

(22) Filed: Feb. 13, 2004

(65) Prior Publication Data

US 2004/0162346 A1 Aug. 19, 2004

Related U.S. Application Data

(63) Continuation of application No. 10/268,069, filed on Oct. 7, 2002, now Pat. No. 6,693,133.

(51) Int. Cl.
*A61K 31/70* (2006.01)
*A61K 31/44* (2006.01)
*A61K 31/19* (2006.01)
*A61K 31/135* (2006.01)

(52) U.S. Cl. ............ 514/25; 514/336; 514/557; 514/647; 514/652; 514/653

(58) Field of Classification Search .............. None
See application file for complete search history.

(56) References Cited

U.S. PATENT DOCUMENTS

| | | | |
|---|---|---|---|
| 5,643,951 A | 7/1997 | Stacpoole et al. | ..... 514/557 |
| 6,076,528 A | 6/2000 | Marangos et al. | |
| 6,423,705 B1 | 7/2002 | Tracey et al. | |
| 6,693,133 B1 | 2/2004 | Lopaschuk et al. | ..... 514/557 |

FOREIGN PATENT DOCUMENTS

| WO | WO95/31986 | 11/1995 |
|---|---|---|
| WO | WO99/17763 | 4/1999 |

OTHER PUBLICATIONS

Agbenyega, T., et al., Population kinetics, efficacy, and safety of dichloroacetate for lactic acidosis due to severe malaria in children, J. Clin. Pharmacol. 43:386-396 (2003).
Allard, M.F., et al., Contribution of oxidative metabolism and gycolysis to ATP production in hypertropied hearts, Am. J. Physiol., 267(2 Pt 2):H742-50 (1994).
Bersin, R.M., et al., Dichloroacetate as metabolic therapy for myocardial ischemia and failure, Am. Heart J., 134(5 Pt 1):841-55 (1997).
Bersin, R.M., et al., Improved hemodynamic function and mechanical efficiency in congestive heart failure with sodium dichloroacetate, J. Am. Coll. Cardiol., 23(7):1617-24 (1994).
Burns, A.H., et al., Inotropic interactions of dichloroacetate with amrinone and ouabain in isolated hearts from endotoxin-shocked rats, J. Cardiovascular Pharmacology, 11:379-386 (1988).
Chang, M.C., et al., Redefining cardiovascular performance during resuscitation: ventricular stroke work, power,and the pressure-volume diagram, J. Trauma, 45(3):470-8 (1998).
Collins-Nakai, R.L., et al., Dichloroacetate acid (DCA) after open heart surgery in infants and children, Canadian Journal of Cardiology, Pulsus Group, Inc., XX, 11(106E):148 (1995).
Currie, P.F., et al., Immunopathogenesis of HIV-related heart muscle disease: current perspectives, AIDS, 17 (suppl. 1)):S21-S28 (2003).
Gamble, J., et al., Glycolysis and glucose oxidation during reperfusion of ischemic hearts from diabetic rats, Biochim. Biophys Acta, 1224(2):191-9 (1994).
Gargaglioni, L.H., et al., Lactate as a modulator of hypoxia-induced hyperventilation, Respir. Physiol Neurobiol., 138(1):37-44 (2003).
Gutierrez, G., et al., Clinical review: Hemorrhagic shock, Critical Care, 8 (DOI 10.1186/cc2851), date not available.
Hall, J.L., et al., Increased cardiac fatty acid uptake with dobutamine infusion in swine is accompanied by a decrease in malonyl CoA levels, Cardiovascular Research 32:879-885 (1996).
Heckbert, S.R., et al., Outcome after hemorrhagic shock in trauma patients, J. Trauma-Injury Infection & Critical Care, 45(3):545-549 (1998).
Kline, J.A., et al., Activation of pyruvate dehydrogenase improves heart function and metabolism after hemorrhagic shock, J. Mol. Cell Cardiol., 29:2465-2474 (1997).
Kline, J.A., et al., Heart function after severe hemorrhagic shock, Shock, 12(6):454-61 (1999).
Kudej, R.K., et al., Brief increase in carbohydrate oxidation after reperfusion reverses myocardial stunning in conscious pigs, Circulation 106:2836-2841 (2002).
Lipschultz, S.E., et al., Left ventricular structure and function in children infected with human immunodeficiency virus: the prospective P2C2 HIV multicenter study. Pediatric pulmonary and cardiac complications of vertically transmitted HIV infection (P2C2 HIV) study group, Circulation 97(13):1246-56 (1998).
Liu, B., et al., Cardiac efficiency is improved after ischemia by altering both the source and fate of protons, Circulation Research, 79:940-948 (1996).
Liu, Q., et al., High levels of fatty acids delay the recovery of intracellular pH and cardiac efficiency in post-ischemic hearts by inhibiting glucose oxidation, J. Am. Coll. Cardiol., 39:718-25 (2002).
Lopaschuk, G.D., et al., An imbalance between glycolysis and glucose oxidation is a possible explanation for the detrimental effects of high levels of fatty acids during aerobic reperfusion of ischemic hearts, J. Pharmacol. Exp. Ther., 264(1):135-44 (1993).
Lopaschuk, G.D., Alterations in fatty acid oxidation during reperfusion of the heart after myocardial ischemia, Am. J. Cardiol. 80(3A):11A-16A (1997).

(Continued)

*Primary Examiner*—Raymond J Henley, III
(74) *Attorney, Agent, or Firm*—Pillsbury Winthrop Shaw Pittman LLP

(57) ABSTRACT

The present invention provides compositions and methods for maintaining cardiac function by administering dichloroacetate (DCA) in combination with an inotrope.

26 Claims, 14 Drawing Sheets

OTHER PUBLICATIONS

Lopaschuk, G.D., et al. Alterations in myocardial fatty acid metabolism contribute to ischemic injury in the diabetic, Can J. Cardiol., 5(6):315-20 (1989).

Matetsky, S., et al., Acute myocardial infarction in human immunodeficiency virus-infected patients, Arch. Intern Med., 163(4):457-60 (2003).

McVeigh, J.J., et al., Dichloroacetate stimulation of glucose oxidation improves recovery of ischemic rat hearts, Am. J. Physiol. 259:H1079-H1085 (1990).

Nicholl, T.A., et al., Effects of free fatty acids and dichloroacetate on isolated working diabetic rat heart, Am. J. Physiol., 261(4 Pt 2):H1053-9 (1991).

Rozanski, G.J., et al., Gluthathione and $K^+$ channel remodeling in posinfarction rat heart, Am. J. Physiol. Heart Circ. Physiol. 282(6):H2346-H2355 (2002).

Rupp, H., et al., The use of partial fatty acid oxidation inhibitors for metabolic therapy of angina pectoris and heart failure, Herz, 27:621-36 (2002).

Saddik, M., et al., Acetyl-CoA carboxylase regulation of fatty acid oxidation in the heart, J. Biol. Chem., 268(34):25836-25845 (1993).

Southard, S., et al., A—Evaluation of dichloroacetate (DCA) as adjunct therapy in severe malaria POC, Commerce Business Daily Issue of Nov. 5, 1996 PSA #1715, National Institute of Allergy & Infectious Diseases, Contract Management Branch, Solar Building, Room 3C07, 6003 Executive Blvd. MSC 7610, Bethesda, MD 20892-7610.

Stacpoole, P.W., et al., Efficacy of dichloroacetate as a lactate-lowering drug, J. Clin. Pharmacol., 43:683-691 (2003).

Stanley, W.C., et al., Pyruvate dehydrogenase activity and malonyl CoA levels in normal and ischemic swine myocardium: Effects of dichloroacetate, J. Mol. Cell Cardiol., 28:905-914 (1996).

Stanley, W.C., et al., Regulation of energy substrate metabolism in the diabetic heart, Cardiovascular Research, 34:25-33 (1997).

Starc, T.J., et al., Incidence of cardiac abnormalities in children with human immunodeficiency virus infection: The prospective P2C2 HIV study, J. Pediatr. 141(3):327-34 (2002).

Stout, T.T., et al., Electrocardiographic changes in acute malaria, Neth J. Med. 37(3-4):124-8 (1990).

Vary, T.C., et al., Sepsis alters pyruvate dehydrognase kinase activity in skeletal muscle, Mol. Cell Biochem. 198(1-2):113-8 (1999).

Wambolt, R.B., et al. Dichloroacetate improves postischemic function of hypertrophied rat hearts, J. Am. Coll. Cardiol., 36:1378-85 (2000).

Watts, J.A., et al., Metabolic dysfunction and depletion of mitochondria in hearts of septic rats, J. Molecular and Cellular Cardiology, 36:141-50 (2004).

Yan, M., et al., 3-O-methyldobutamine, a major metabolite of dobutamine in humans, Drug Metabolism and Disposition: the Biological Fate of Chemicals, 30(5):519-524 (2002).

Zenati, M.S., et al., A brief episode of hypotension increases mortality in critically III trauma patients, J. Trauma-Injury Infection & Critical Care, 53(2):232-237 (2002).

Figure 1

Pre-op and Post-op Cardiac Medications Used in Adult Coronary Bypass Graft Patients in Study of Example A Example A - DCA administration of a 50mg/kg bolus, post-coronary bypass graft surgery (CABG) increases target heart enzyme activity in adult heart patients as compared to placebo Example A - DCA administration of a 50mg/kg bolus, post coronary bypass graft surgery (CABG) in adult heart patients decreases plasma lactate levels as compared to placebo Example B - DCA administration as a 50kg/mg bolus, post-surgery in pediatric heart patients decreases 1 hour Inotrope Score as compared to placebo Example B - DCA administration as a 50kg/mg bolus post surgery in pediatric heart patients decreases ICU time as compared to placebo Example B - DCA administration as a 50kg/mg bolus, post-surgery in pediatric heart patients decreases ventilator time as compared to placebo

Figure 7A

Administration of Inotrope to patients of the Study of Example C (1 = yes, given; 0 = Not Given)

| Patent No. | Pre-Op Inotrope | Post-Op Inotrope |
|---|---|---|
| 1 | 0 | 0 |
| 2 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |
| 9 | 0 | 0 |
| 10 | 0 | 0 |
| 11 | 0 | 0 |
| 12 | 0 | 0 |
| 13 | 0 | 0 |
| 14 | 0 | 0 |
| 15 | 0 | 0 |
| 16 | 0 | 1 |
| 17 | 0 | 0 |
| 18 | 0 | 0 |
| 19 | 0 | 0 |
| 20 | 0 | 0 |
| 21 | 1 | 0 |
| 22 | 0 | 0 |
| 23 | 1 | 0 |
| 24 | 0 | 0 |
| 25 | 0 | 0 |
| 26 | 0 | 0 |
| 27 | 0 | 0 |
| 28 | 0 | 0 |
| 30 | 0 | 0 |
| 31 | 0 | 0 |
| 32 | 0 | 0 |
| 33 | 1 | 1 |
| 34 | 0 | 0 |
| 35 | 0 | 0 |
| 36 | 0 | 0 |
| 37 | 0 | 0 |
| 39 | 0 | 0 |
| 40 | 0 | 0 |
| 41 | 0 | 0 |

Figure 7A, Page 2

| | | |
|---|---|---|
| 42 | 0 | 0 |
| 44 | 0 | 0 |
| 45 | 0 | 0 |
| 46 | 0 | 0 |
| 47 | 0 | 0 |
| 48 | 1 | 1 |
| 49 | 0 | 0 |
| 50 | 0 | 0 |
| 51 | 0 | 0 |
| 52 | 0 | 0 |

Figure 7B

| Ace Inhibitors | Inotrope | Vasodilator | Diuretic | Beta-Blocker | Anticoagulant | Heparin or Enoxaprin Sodium | Analgesic |
|---|---|---|---|---|---|---|---|
|  | Dobutamine | Prostin | Lasix | Propronalol | Coumadin | Lovenex | Aspirin |
| Captropril | Epinephrine |  | Aldactazide | Atenolol |  | Enoxapram | Tylenol |
| Fosinopril | Dopamine |  | Ranitidine |  |  |  |  |
| Enlapril | Norepinephrine |  |  |  |  |  |  |
|  | Phenylephrine |  |  |  |  |  |  |
|  | Phenatalomine |  |  |  |  |  |  |
|  | Amironone |  |  |  |  |  |  |
|  | Digoxin |  |  |  |  |  |  |

Figure 8

Example C - Effects of DCA administration as a 50mg/kg bolus and 25mg/kg/hour infusion, post-heart surgery in pediatric heart patients reduces Inotrope Score over 24 hours as compared to placebo

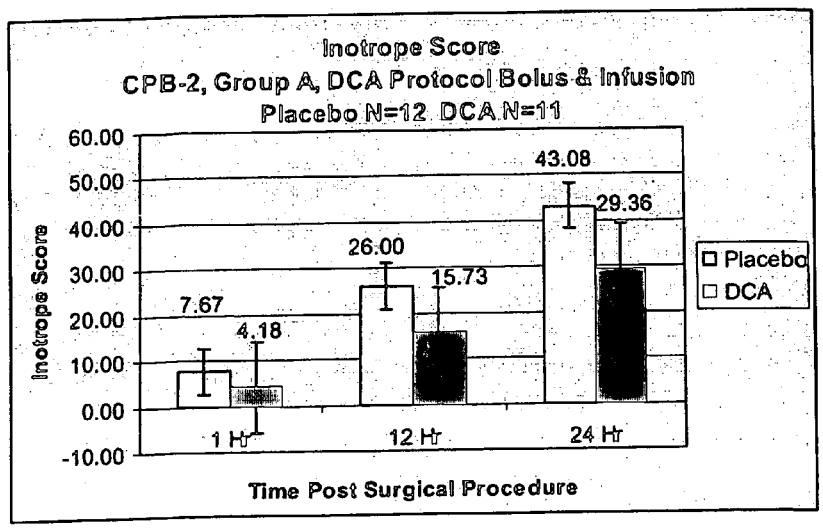

Example C - Effects of DCA administration as a 100mg/kg bolus and 12.5mg/kg/hour infusion, post-surgery in pediatric heart patients reduces Inotrope Score over 24 hours as compared to placebo Example C - Effects of DCA administration as a 50mg/kg bolus and 25mg/kg/hour infusion, post-surgery in pediatric heart patients reduces ICU Time as compared to placebo Example C - Effects of DCA administration as a 100mg/kg bolus and 12.5mg/kg/hour infusion post-surgery in pediatric heart patients reduces ICU Time as compared to placebo Example C - Effects of DCA administration as a 50mg/kg bolus and 25mg/kg/hour infusion, post-surgery in pediatric heart patients reduces Ventilator Time as compared to placebo Example C - Effects of DCA administration as a 100mg/kg bolus and 12.5mg/kg/hour infusion post-surgery in pediatric heart patients reduces Ventilator Time as compared to placebo

METHODS OF CARDIOPROTECTION USING DICHLOROACETATE IN COMBINATION WITH AN INOTROPE

CROSS-REFERENCE TO RELATED APPLICATIONS

This application is a continuation of U.S. application Ser. No. 10/268,069, filed Oct. 7, 2002, now U.S. Pat. No. 6,693,133, the entire contents of which is incorporated herein by reference.

BACKGROUND AND INTRODUCTION TO THE INVENTION

There is a need for methods of protecting the heart from injury, which may occur due to ischemic incidents and during reperfusion following ischemia, and maintaining cardiac function at a predetermined level thereafter.

Clinically, ischemia-reperfusion may occur in the setting of cardiac surgery. In order to perform many surgical procedures it is necessary to interrupt coronary blood flow resulting in ischemia to the heart. This ischemia not only limits the time available for the surgical procedure, it can also result in contractile dysfunction upon restoration of coronary flow. This is not only a problem in the adult patient undergoing coronary artery bypass surgery (CABG) or other surgical procedures, it is also a significant clinical problem during surgical heart procedures to correct congenital heart defects in neonates.

Current therapies aimed at improving contractile function following cardiac surgery in adult, pediatric and neonatal patients often involve the use of inotropes (e.g., calcium, dopamine, epinephrine, ephedrine, phenylephrine, dobutamine) in an attempt to increase contractile function. Although inotropic agents such as dobutamine have been reported to increase myocardial stroke volume and work, they also have been reported to increase myocardial oxygen consumption, and therefore may not enhance mechanical efficiency (1). In fact, the potential for inotropes to increase oxygen consumption to a greater extent than contractile function has been termed an oxygen wasting effect (2, 3). Inotropic drugs are also reportedly associated with increases in intracellular calcium concentration and heart rate, which may also be potentially harmful, especially in hearts with impaired energy balance (4).

SUMMARY OF THE INVENTION

The present invention is directed to methods of maintaining and improving cardiac function during and following an ischemic event and during reperfusion by administration of dichloroacetate ("DCA") in combination with an inotrope. According to one aspect the methods of the present invention improve cardiac functional recovery and metabolism after an ischemic event, such as surgical heart procedures (including cardiopulmonary bypass and congenital lesions) in patients, as well as cardiovascular disorders such as hemorrhagic shock, hypoxia and trauma.

According to an aspect of the present invention, combination therapy of DCA with inotropes will enable administration of a lower dose of inotrope needed to maintain contractile function post-surgery.

One aspect of the present invention is directed to a method of decreasing the amount of inotrope needed to maintain a predetermined level of cardiac function in a patient which comprises administering to said patient a cardioprotective amount of dichloroacetate (DCA). According to this aspect, DCA may be administered as a bolus of at least about 50 mg/kg. According to one embodiment, administration of the DCA bolus is followed by an infusion of about 12.5 mg/kg/hour DCA for at least about 24 hours.

According to another aspect of the present invention, provided is a method of maintaining cardiac function at a predetermined level in a patient after cardiac surgery and decreasing said patient's need for inotropes which comprises administering to said patient DCA in a bolus of at least 50 mg/kg followed by infusion of at least about 12.5 mg/kg/hour for at least about 24 hours.

In an alternate aspect, the present invention provides an improved method of maintaining cardiac function at a predetermined level in a patient in need of treatment while decreasing inotrope requirements, wherein the improvement comprises administering DCA within 15 minutes of administering said inotrope.

In another aspect, the present invention is directed to a method of decreasing the inotrope score in a patient who has undergone cardiac surgery which comprises administering a cardioprotective amount of DCA.

Please note that while the present invention is not limited to a particular dose level of DCA, doses and dosing protocols are suitable for use according to the methods of the present invention include the following. According to one aspect, DCA is administered continuously and a plasma level of at least about 1 mM is maintained in the patient for at least about 24 hours. According to one embodiment, a plasma level of at least about 1 mM, alternatively from about 1 mM to about 2 mM is maintained. The plasma level is maintained for at least about 1 hour, alternatively at least about 24 hours. According to an aspect of this embodiment, DCA is administered as a bolus before beginning the continuous administration of DCA. Suitable bolus doses are at least about 50 mg/kg, alternatively at least about 100 mg/kg. Suitable dose ranges for the bolus include at least about 50 mg/kg, alternatively from about 50 mg/kg to about 100 mg/kg.

The present invention provides DCA and inotrope to be administered in combination with each other, as in a single solution comprising DCA and inotrope. This combination method of administration allows decreasing the inotrope score in a patient who has undergone cardiac surgery wherein DCA is administered in a cardioprotective amount. In a further aspect of the invention, the method entails the administration of a bolus of DCA as described herein followed by administration of the combination intravenously, such as by intravenous infusion.

According to another aspect of the invention, provided is a pharmaceutical combination comprising a cardioprotective amount of DCA and an inotrope, the inotrope may be present at a therapeutically effective concentration to provide a lower dose of inotrope than the dose of inotrope that would be therapeutically effective in the absence of DCA.

Definitions:

"Inotrope" or "inotropic drugs" refers to a class of pharmaceutical agents which increase the contractility of cardiac muscular action. Inotropes conventionally used to maintain cardiac function and contractility include dobutamine, epinephrine, dopamine, norepinephrine, phenylephrine, phentolamine, digoxin, amrinone, and other agents known to those in the art.

BRIEF DESCRIPTION OF THE DRAWINGS

FIG. 1 depicts a chart noting the pre-op and post-op cardiac medications used for the patients in the study described in Example A.

FIG. 7A depicts a summary of patients in the study of Example C treated pre-op or post-op with inotropes.

FIG. 7B depicts a list of hemodynamic drugs routinely administered pre-op or post-op to cardiac surgery patients such as the patients of the studies described in Examples B and C.

FIG. 8 depicts a graph of the effects on inotrope score of administration of a 50 mg/kg bolus of DCA followed by a 25 mg/kg/hour infusion versus placebo in post-heart surgery patients. See Example C.

DETAILED DESCRIPTION OF THE INVENTION

Cardiac Metabolism

Figure 2:
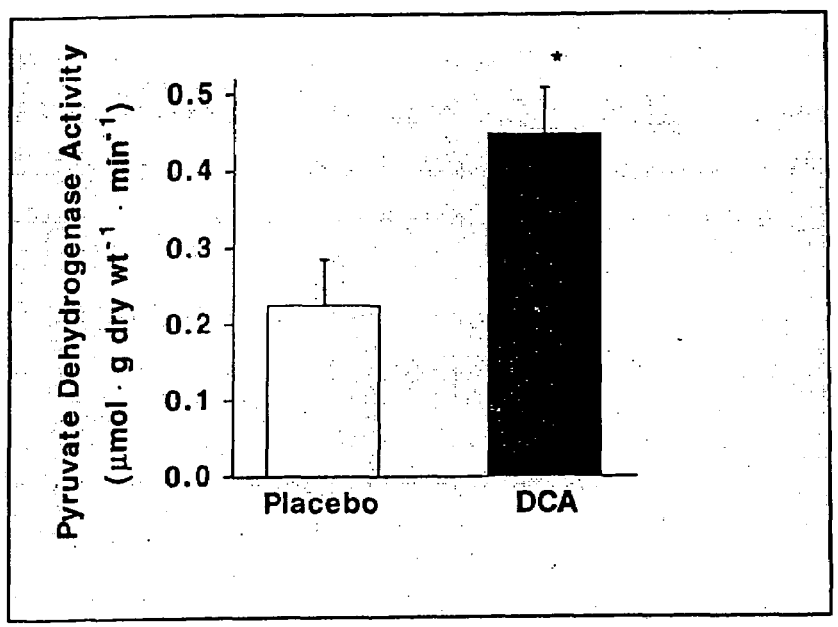
FIG. 2 depicts a graph of pyruvate dehydrogenase activity (PDH) after administration of a 50 mg/kg bolus of DCA or placebo. See Example A.

Under normal aerobic conditions, oxidation of fatty acids is the predominant source of energy (ATP) production in the heart, with a lesser contribution being derived from lactate and glucose. However, during ischemia (such as occurs during cardiac surgery), when the supply of oxygen becomes limiting, anaerobic glycolysis assumes a more important role, and fatty acid and carbohydrate oxidation decrease (5, 6). During reperfusion following ischemia, ATP production, tricarboxylic acid (TCA) cycle activity and oxygen consumption rapidly recover. Fatty acid oxidation also quickly recovers providing over 90% of the overall ATP production (7, 8). The reason for this increase in fatty acid oxidation is reportedly due both to ischemic-induced alterations in the control of myocardial fatty acid oxidation (9, 10), as well as an increase in circulating fatty acid levels (11, 12). The use of inotropes with adrenergic agonist properties can also contribute to these high plasma levels of fatty acids. This excessive use of fatty acids by the heart following ischemia can have adverse effects on both cardiac function and cardiac efficiency.

The availability of different energy substrates and the type of energy substrate used by the heart can have profound effects on cardiac functional recovery during and following an ischemic episode. Specifically, high rates of fatty acid oxidation may contribute to a marked decrease in cardiac efficiency secondary to inhibition of glucose oxidation (5, 6, 7). However, if glucose oxidation is stimulated during reperfusion, a significant increase in cardiac efficiency results, with a parallel improvement in cardiac function (11). This is partly due to a decreased requirement of oxygen to produce equivalent amounts of ATP (7, 13). Stimulating glucose oxidation also decreases the production of protons in the heart, therefore decreasing the amount of ATP necessary to maintain ionic homeostasis in the heart.

In fetal life, glycolysis and lactate oxidation are the major sources of ATP production. However, following birth there is a rapid maturation of fatty acid oxidation, which rapidly becomes the predominant source of ATP production in the newborn heart (13, 19, 20). Under aerobic conditions, glucose oxidation rates are lower in neonatal hearts compared with adult hearts (21, 22). Simultaneous measurement of both glycolysis and glucose oxidation in neonatal hearts has demonstrated that glycolytic rates are much greater than rates of glucose oxidation, suggesting low flux through pyruvate dehydrogenase (PDH), the rate-limiting enzyme for glucose oxidation (21). Therefore, when the newborn heart is subjected to ischemia-reperfusion injury during open heart surgery, the increase in fatty acid oxidation may be particularly detrimental, since the glucose oxidation pathway in these hearts has not completely matured. Studies in immature rabbit hearts have shown that addition of pyruvate, a substance that stimulates PDH activity, significantly increases aortic flow, cardiac work, and developed pressure (23). Based on these studies, we believe that a metabolic therapy, which stimulates glucose oxidation at the expense of fatty acid oxidation, would enhance cardiac recovery following ischemia.

Cardioprotective Effects of Dichloroacetate on the Heart

We have found dichloroacetate (DCA) to be particularly effective at stimulating glucose oxidation in the heart. DCA has been reported to stimulate pyruvate dehydrogenase (PDH), the rate-limiting enzyme for glucose oxidation in the heart (14, 15). This stimulation appears to occur via DCA inhibition of PDH kinase, which normally phosphorylates and inhibits PDH. In experimental studies on isolated rat hearts, we showed that DCA dramatically improves functional recovery and cardiac efficiency during reperfusion of hearts following a severe episode of ischemia (9, 16, 17). This beneficial effect of DCA is due to a dramatic stimulation of glucose oxidation and a switch in energy substrate use by the heart from fatty acid oxidation towards glucose metabolism (15, 7). DCA also dramatically decreases proton production in the reperfused ischemic heart, which is a major reason for the DCA-induced improvement in cardiac efficiency during reperfusion (16).

Since DCA has demonstrated such dramatic effects in our studies on cardioprotective effects on the ischemic. heart, it may be of clinical use in maintaining and improving cardiac function (including contractility) in the setting of cardiac surgery both for the adult and pediatric patient. Plasma levels of fatty acids have been observed to increase significantly during reperfusion following cardiac surgery. This increase is observed to be highest in pediatric patients, including patients as young as three weeks of age (10). Elevations in free fatty acids may result in an increase in myocardial oxygen consumption, which may potentiate ischemic injury (11).

Inotropes are frequently administered to patients to improve contractile function of the heart following cardiac surgery. However, some effects of inotropes may not be desirable. For example, epinephrine, an inotropic agent, has been reported to increase the uncoupling between glycolysis and glucose oxidation resulting in a significant increase in proton production from glucose metabolism (24). This potentially may accelerate acidosis during the reperfusion period, at a time when the heart is trying to clear a preexisting proton load produced during ischemia, and would be another undesirable effect of inotrope use (8, 1).

While not wanting to be bound to a particular theory, we believe that by stimulating glucose oxidation, administration of DCA lessens the need for inotropes (or dose of inotrope) and other hemodynamic drugs used post-operatively. We have shown that DCA is cardioprotective in adults, pediatric patients, and neonates undergoing open heart cardiac surgical procedures. The present examples describe studies that determine that DCA when used in combination with inotropes lessens the dose of inotrope needed.

In one aspect, the present invention is directed to the use of dichloroacetate (DCA) to improve cardiac functional recovery and metabolism after open heart surgical procedures (cardiopulmonary bypass and congenital lesions) in patients and to decrease the need for administering of inotropes and if inotropes are administered, decrease the dose of inotrope needed to maintain cardiac function (including contractility) at a desired predetermined level. Administration of DCA lessens the need for inotropes and other hemodynamic agents. As a result, combination therapy with DCA will allow for a lowering of the amount and doses of inotropes used.

We believe that pediatric patients receive even greater benefits from DCA during cardiac surgery because, as previously noted, they have the highest fatty acid levels during and after cardiac surgery accompanied by the lowest rates of glucose oxidation. In a study of 40 pediatric patients (age 0.03-15.1 years) requiring open heart surgery (see Example B), DCA was given as a bolus dose of 50 mg/kg into the aortic root just prior to the release of the cross clamp. One-hour Inotrope Score was significantly lower in the DCA group compared to placebo (which indicated better cardiac function). ICU days and ventilator hours were also lower in the DCA group. This study demonstrated that DCA, when used in combination with inotropes, will lessen the requirements for inotropes in the immediate post-surgery period.

Use of DCA as a Cardioprotective Agent and to Decrease the Need for Inotropes

The studies described in Example A demonstrate that DCA administration increases PDH activity in the human heart and improves carbohydrate oxidation.

In Example A, studies in 18 adult Coronary Artery Bypass Graft (CABG) patients demonstrated that giving DCA as a bolus was effective in producing the desired metabolic effects of DCA. Cardiac PDH enzyme activity following surgery was increased significantly following administration of DCA. As well, DCA also significantly decreased plasma lactate levels.

In the studies described in Examples B and C we observed that DCA administered as a bolus dose post-surgery to pediatric patients undergoing cardiac surgery significantly lowered the dose of inotropes required to sustain contractile function and decreased the time spent in the Intensive Care Unit (ICU).

When DCA was administered using a bolus and infusion protocol to maintain therapeutic levels of DCA over a 24 hour period during reperfusion for surgical heart procedures, the therapeutic benefits of DCA were sustained in the presence of other clinically recommended hemodynamic drugs, the requirements for inotropes were decreased, and the patients' time spent on the ventilator and in the ICU was significantly decreased.

In Example B, where DCA was administered as a bolus dosing protocol, the clinical benefit of DCA was demonstrated in a study which consisted of a 40 pediatric patients study for surgical heart procedures. Data from this trial revealed that patients treated with DCA had a significantly reduced Inotrope Score, had reduced time in ICU and had reduced time on the ventilator as compared to patients treated with placebo. The results observed after administration of DCA as a bolus of 50 mg/kg in the study described in Example B encouraged us to proceed with the DCA protocol used for the study described in Example C.

A dose range for DCA of about 1 mM has been shown to be effective in increasing PDH levels and improving myocardial function in isolated perfused hearts. (This dose range was also supported by data from the study described in Example A using a bolus administration of 50 m/kg DCA.) The bolus and infusion administration in the study described in Example C provided the therapeutic benefits of DCA at a DCA therapeutic level in blood plasma of 1 mM (7, 9, 16, 17) during the critical 24 hour period post-surgery. Using a bolus and infusion protocol, data from the study described in Example C (which consisted of 51 pediatric patients) revealed that such treatment resulted in a reduced need for inotropic drugs. (As noted in Example C, the final results were based on 47 patients, 51 patients less 4 infusion pump failure cases).

In the study described in Example C, the DCA protocols used two different dosing administrations in the presence of clinical recommended therapeutic levels of hemodynamic drugs: Group A was originally given a bolus of 50 mg/kg and an infusion of 25 mg/kg/hr; and Group B was given a bolus of 100 mg/kg and an infusion of 12.5 mg/kg/hr. (The cardiac surgeon in the study described in Example C had good results and therefore used less inotropes to maintain cardiac index in all patients.)

In the study described in Example C, the DCA therapeutic range level of the DCA patients in both Groups A and B, showed benefits at DCA therapeutic plasma levels 0.229 mM to 2.22 mM at the 1 to 6 hour interval, and from 1.74 mM to as high as 3.9 mM at the 24 hour interval (Table I). There were 11 DCA patients in each of Groups A and B, and noted below in Table I as n=the number of DCA patients where the DCA blood plasma levels measured at each interval.

TABLE I

| | Average DCA Plasma Levels (Example C) | | | |
|---|---|---|---|---|
| | mM at 1 hr | mM at 6 hr | mM at 12 hr | mM at 24 hr |
| Group A 50 mg/kg bolus and 25 mg/kg/hr infusion | .460 (n = 11) | 1.134 (n = 10) | 1.771 (n = 9) | 2.724 (n = 11) |
| Group B 100 mg/kg bolus and 12.5 mg/kg/hr infusion | 1.131 (n = 11) | .894 (n = 11) | 1.427 (n = 11) | 2.231 (n = 10) |

The DCA therapeutic optimum means for the different intervals from the study described in Example C were based on the DCA patient outcomes with the greatest degree of clinical benefits (cardiac index, ICU and ventilator time) as compared to placebo. These DCA plasma range outcomes were from both the simple open heart surgery and complex open heart surgery patients—at the 1 hour interval from Group B, and at the 12 and the 24 hour intervals from Group A. The optimum DCA therapeutic dose level average means are as summarized below in Table II.

TABLE II

Average Optimum Mean of DCA Plasma Levels (Example C)
Group A and Group B n = data from DCA patients numbers with
Greatest Degree of Clinical Benefits

|  | mM at 1 hr | mM at 6 hr | mM at 12 hr | mM at 24 hr |
|---|---|---|---|---|
| Group A 50 mg/kg bolus and 25 mg/kg/hr infusion | 1.0 | 0.916 (m = 5) | 1.523 (m = 5) | 2.288 (m = 6) |
| Group B 100 mg/kg bolus and 12.5 mg/kg/hr infusion | 1.012 (n = 7) | 1.0 | 1.0 | 1.0 |

The known DCA therapeutic dose level mean of 1 mM was observed in Group B at the 1 to 6 hour interval. (with a DCA plasma level range of 0.229 mM to 2.22 mM) A different optimum DCA therapeutic dose level at 2.29 mM means was observed from Group A at the 24 hour period (with a DCA plasma level range of 1.73 mM to 3.91 mM).

Figure 10:
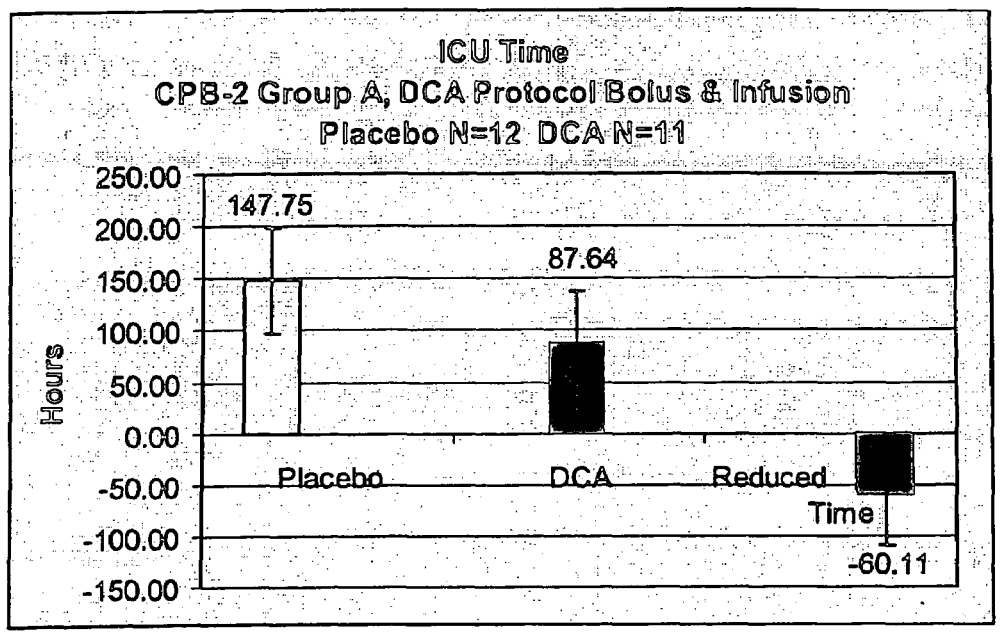
FIG. 10 depicts a graph of effects on reducing ICU time of DCA administration as a 50 mg/kg bolus and 25 mg/kg/hour infusion post-surgery in patients as compared to placebo. See Example C.
Figure 12:
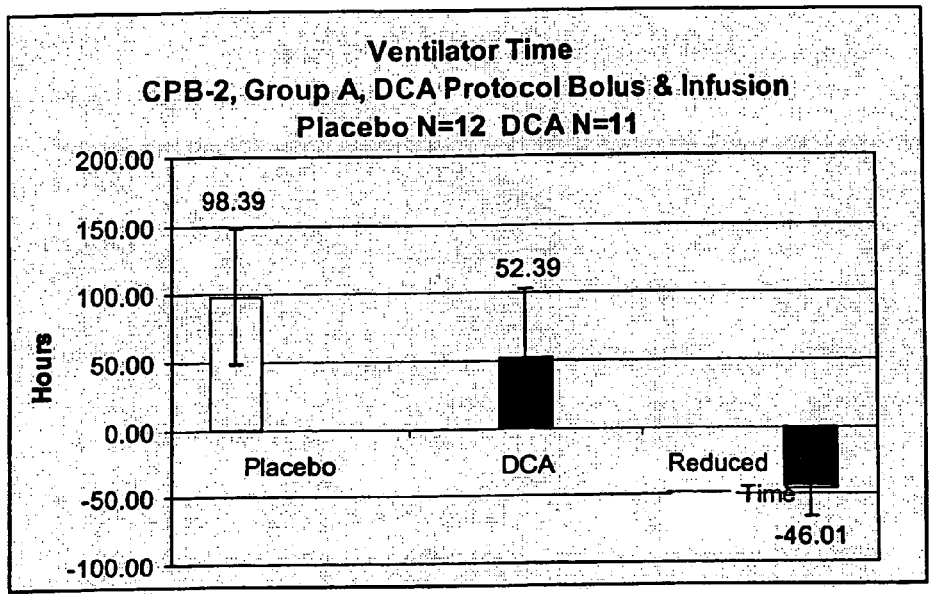
FIG. 12 depicts a graph of the effects on reducing ventilator time for patients with DCA administration as a 50 mg/kg bolus and 25 mg/kg/hour infusion post-surgery as compared with placebo. See Example C.

The resulting data in the Group A protocol of a bolus of 50 mg/kg and an infusion of 25 mg/kg/hour post-surgical heart procedure for 23 patients reduced the time in ICU (FIG. 10) post-surgical procedure by 60 hours (a 41% decrease) as compared to placebo. The reduction of Inotrope Scores (FIG. 8) was by 1 hour at a 50% decrease, and by 12 hours at a 45% decrease and by 24 hours at a 38% decrease as compared to placebo. Ventilator time (FIG. 12) was reduced by 46 hours (a 47% decrease) as compared to placebo.

Figure 9:
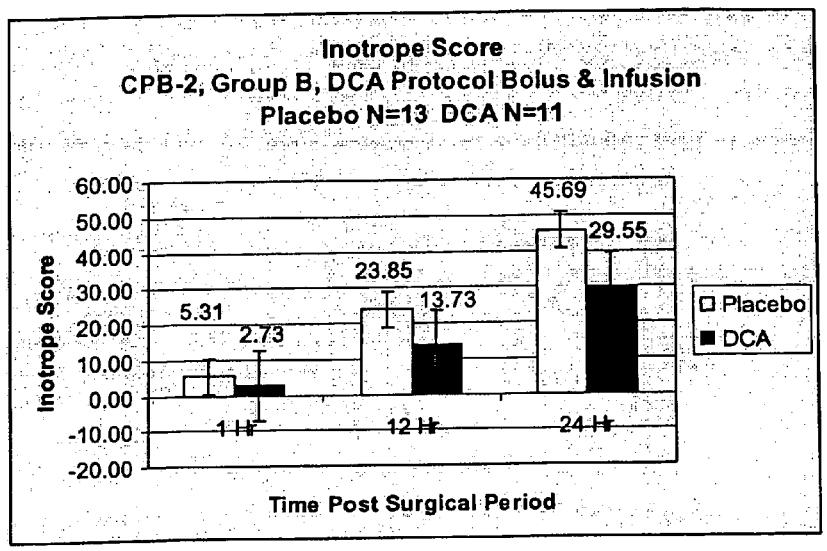
FIG. 9 depicts a graph of the effects on inotrope score of DCA administration as a 100 mg/kg bolus and 12.5 mg/kg/hour infusion versus placebo post-surgery in pediatric patients. See Example C.
Figure 11:
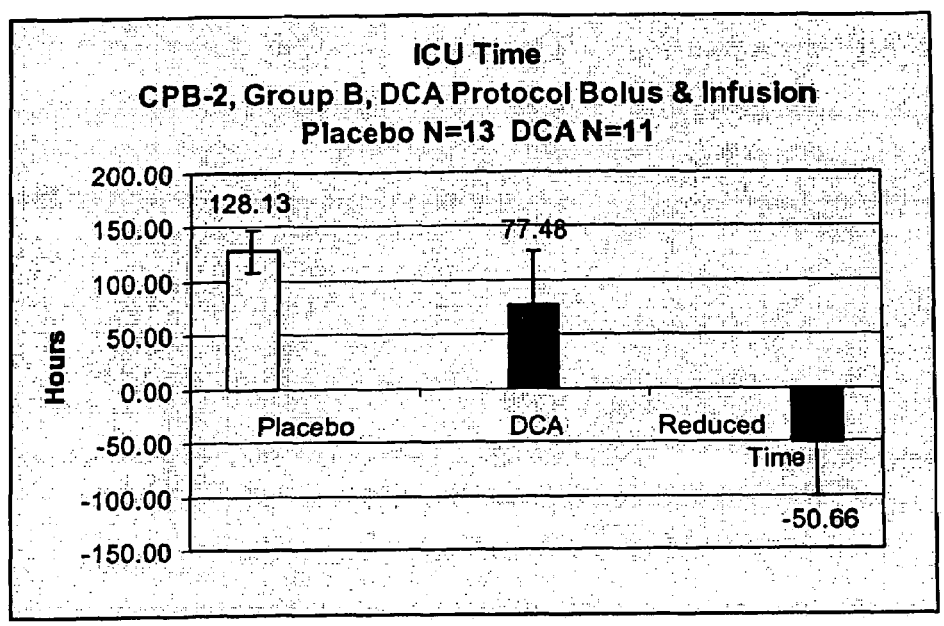
FIG. 11 depicts a graph of the effects on reducing ICU time for patients with DCA treatment as 100 mg/kg bolus and 12.5 mg/kg/hour infusion post-surgery as compared with placebo. See Example C.
Figure 13:
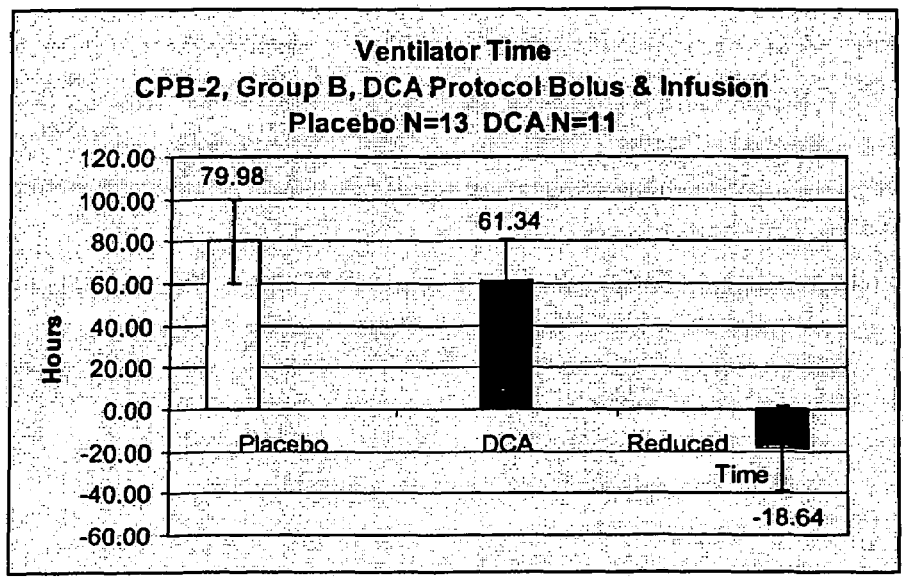
FIG. 13 depicts a graph of the effects on ventilator time for patients with DCA treatment as a 100 mg/kg bolus and 12.5 mg/kg/hour infusion post-surgery as compared to placebo. See Example C.

The resulting data in the Group B protocol of a bolus of 100 mg/kg and an infusion of 12.5 mg/kg/hour, post-surgical heart procedure for 24 patients, reduced the time in ICU (FIG. 11), post surgical procedure over the 24 hour period by 50 hours (a 40% decrease) as compared to placebo. The reduction of Inotrope Scores (FIG. 9) averaged by 1 hour at a 57% decrease, and by 12 hours at a 49% decrease, and by 24 hours at a 45% decrease as compared to placebo. Ventilator Time (FIG. 13) was reduced by 19 hours (a 23% decrease) as compared to placebo.

The merit of reducing inotropic drugs with the bolus and infusion administration of DCA is supported by the data from the 1 hour period through the 24 hour period post surgical heart procedures from the study described in Example C.

The data measurement outcomes from in vitro modeling testing (17) indicate that the administration of DCA at a constant therapeutic level of 1 mM maintains its benefits in the presence of clinically high levels of hemodynamic drugs. Administering a constant optimum therapeutic mean level (based on the optimum outcome) of DCA observed in the presence of clinically acceptable lower levels of hemodynamic drugs will provide significant cardioprotective benefits and decrease deleterious effects which may occur with use of such hemodynamic agents. In the studies described in the Examples, we found optimum mean levels for DCA plasma ranges at specific intervals were as to include: 1 mM (0.229 mM to 2.22 mM DCA plasma range) during the 1 to 6 hour period, 1.52 mM (0.38 mM to 3.07 mM plasma range) at the 12 hour interval, and 2.29 mM (1.73 mM to 3.91 mM DCA plasma range) at the 24 hour interval.

Taken together, improving cardioprotective benefits, and improved cardiac function were maintained by using DCA at a constant therapeutic level of about 1 mM in the presence of clinically recommended dose levels of hemodynamic drugs over a 24 hour period. In the presence of clinically high levels of hemodynamic drugs, by using our DCA protocol to maintain a constant therapeutic range of 1 mM at the 1 to 6 hour period, 1.5 mM at the 12 hour interval, and 2.29 mM at the 24 hour interval, improving cardioprotective benefits, and improved cardiac function are also maintained.

Administration and Dosing of DCA

While it is not intended that the present invention be limited by the particular delivery means, one delivery means is an intravenous means, such as that achieved by introduction through an intravenous drip. Other means includes (but is not limited to) delivery with a catheter. Another means involves direct injection into the aorta, for example, with a catheter. Still other routes of administration include subcutaneous, sublingual and oral routes to achieve a decrease in the amount of inotrope needed to maintain a predetermined level of cardiac function.

The particular dosage of DCA is also not intended to be limiting. A variety of temporal protocols is contemplated. Delivery in a bolus as well as continuous delivery is contemplated. In one embodiment, DCA (such as sodium dichloroacetate) is given in a bolus of at least 100 mg/kg of an approximately 100 mg/ml solution (1.0 cc/kg bolus) and, immediately thereafter, dichloroacetate is given as an infusion at approximately 12.5 mg/kg/hr for greater than 10 hours, and more preferably, 24 hours or more.

According to one aspect of the present invention, DCA is administered to a patient under conditions such that said subject has a blood (e.g., serum or plasma) concentration of DCA of greater than approximately 200 µM, alternatively greater than 500 µM, and even greater than 1 mM, for a period of time longer than 1 hour, alternatively longer than 6 hours, and even 24 hours or longer. In one embodiment, DCA is delivered as a bolus, followed by continuous administration.

Higher dosages than those noted above may be used. We have observed DCA to not have significant side-effects, although some patients experience mild drowsiness.

To assist in understanding, the present invention will now be further illustrated by the following Examples. These Examples as they relate to the present invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Methods Used in the Studies Described in Examples A to C

The studies described in Examples A to C describe three different clinical studies of the effect of DCA when administered to patients during and/or following cardiac surgery.

The study described in Example A involved adult patients in which the effects of DCA on cardiac metabolism were studied. DCA was administered to patients undergoing elective cardiac bypass grafting surgery (CABG). This study was performed in the presence of clinically recommended dosages of hemodynamic drugs in coronary artery bypass grafts.

The study described in Example B involved the administration of a single bolus dose of DCA to pediatric patients undergoing cardiac surgery to correct congenital heart lesions. This protocol, performed in the presence of clinically recommended hemodynamic drugs, determined that the dose and amount of these agents could be decreased with DCA use.

The study described in Example C involved the use of a bolus and infusion protocol to administer DCA over a 24 hour period to pediatric patients undergoing cardiac surgery to correct congenital heart lesions. This protocol was also performed in the presence of clinically recommended hemodynamic drugs, and determined that the dose and amount of these agents could be decreased with DCA use.

Example A

Description of Study Protocol

DCA or saline was administered to 18 patients undergoing elective cardiac bypass grafting surgery (CABG) in a double blinded randomized manner DCA (50 mg/kg in 100 ml of saline) or placebo was injected into the aortic root, immediately prior to removing aortic cross clamp. Based on the pharmacokinetics of DCA, we anticipated that this would produce a plasma concentration of approximately 1 mM. The study consisted of 8 DCA-treated patients and 10 placebo-treated patients.

1. Intervention
   a. "Usual" Therapy
   All procedures and drugs normally given for CABG patients were given routinely. A list of medications provided for these patients shown in FIG. 1.
   b. "Intervention" Therapy
   The intervention involved DCA (50 mg/kg) or placebo injected into the aortic root immediately prior to removing aortic cross clamp. The coded solution was made such that a dose of 1 ml/kg provides the appropriate dose of DCA or placebo. Based on the pharmacokinetics of DCA, this was expected to result in a plasma level of DCA in the therapeutic range of (1 mM). All blood samples were analyzed by HPLC for DCA concentration.

2. Sample Processing
   Plasma samples were processed for DCA levels using a high performance liquid chromatography (HPLC) technique that separated the DCA from other plasma constituents. In brief, 20 µl of plasma sample was injected into a Beckman Gold HPLC containing a IonoBpher 5A column (250×4.6 mm LxID) and a AX Guard Column. The mobile phase of the column consisted of 10-3 M pyromellitate buffer (pH=4.0). The flow rate of the HPLC was set at 3.0 ml/min and the DCA eluted from the column was detected by comparing DCA elution times to acetate, monochloroacetate, and trichloroacetate standards. Heart ventricular biopsy samples were taken at 0, and 20 minutes, and at 1 hour, following release of the cross clamp and reperfusion of the heart muscle, and immediately frozen in liquid $N_2$. Blood samples were also taken at various intervals during the reperfusion period between 0 to 24 hours post-surgery.
   PDH activity was measured in ventricular biopsies using a radioisotope procedure which determines the production of 14C-citrate formed from 14C-oxaloacetate and acetyl CoA derived from PDH (8). Blood levels of lactate, fatty acids and glucose were measured using standard enzymatic assays.

3. Statistical Analysis
   Comparisons of demographics between groups were done using unpaired t-tests (continuous variables) and Chi-square tests (discrete variables). Comparison of cardiac index between groups was done using a nonparametric unpaired test. Statistical significance is defined as $p<0.05$. Data handling and statistical analysis was performed by the Epicore Center at the University of Alberta.

Results of Study

Figure 3:
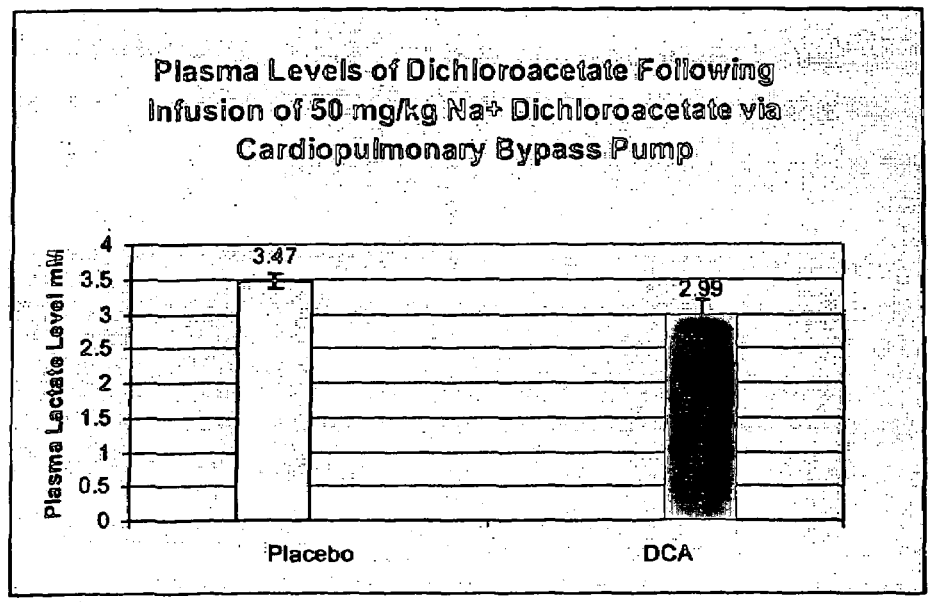
FIG. 3 depicts a graph of plasma levels of acetate following infusion of placebo or 50 mg/kg DCA via cardiac bypass pump in the study of Example A.

In this study in 18 adult cardiovascular surgery patients, DCA was administered as a bolus dose of 50 mg/kg to 8 adult patients in the presence of other clinically recommended doses of hemodynamic drugs (FIG. 1). DCA was administered immediately prior to restoration of coronary blood flow following the cardiac procedure. In patients treated with DCA, compared to placebo, there was a significant increase in PDH activity in heart muscle biopsies taken in the early reperfusion period (FIG. 2). DCA also significantly decreased lactate levels (FIG. 3), indicating that DCA increases carbohydrate oxidation during reperfusion. There was a single mortality in the placebo group and no mortalities the DCA group.

Plasma levels of DCA were also measured in patients at 1 hour following administration of DCA. Plasma levels of DCA were approximately 1 mM, a concentration we have shown to be efficacious in stimulating glucose oxidation in experimental animal studies (9, 16).

TABLE III

Plasma Levels of Dichloroacetate Following Infusion of 50 mg/kg
$Na^+$ Dichloroacetate via Cardiopulmonary Bypass Pump
Plasma Dichloroacetate Levels
(mM) (n = 8)

| 0.948 ± 0.061 |
|---|

Combined, the data in this study of adult patients demonstrated that our dosing protocol: 1) resulted in a therapeutic level of DCA in the critical early period of reperfusion post cardiac surgery, and 2) this dose of DCA increased cardiac PDH activity and lowers circulating plasma lactate levels.

Example B

Description of Study Protocol

This study was a randomized, placebo-controlled, double blinded, single surgeon, study of the use of DCA in 40 high-risk pediatric patients requiring heart surgery to connect complex congenital heart lesions.

1. Study Population
   In this trial, 40 children were recruited to participate in a single surgeon study, of which 18 received DCA and 22 received placebo. The 1995 power calculations were based on separation of the CPB-1 trial of n=40 patients.

2. Inclusion Criteria
   a. Age less than 1 year.
   b. Consent from parent or guardian.
   c. Requirement for open-heart surgery to correct complex congenital heart lesions (e.g., such as Tetralogy of Fallot).
   d. Agreement of the surgeon, anesthetist and cardiologist.
   e. Significant non cardiac complications precluding study protocol implementation.

3. Exclusion Criteria
   a. Lack of parental consent.
   b. Refusal for entry from surgeon or anesthetist or cardiologist 4. Randomization, Data Collection, and Blinding Procedures Computerized randomization of study medications were performed by the Epicore Centre at the University of Alberta. The patients and all study personnel were blinded throughout the study. Unblinding was set into the procedures only if, in the opinion of the patient's physician or study personnel, information concerning the identity of the study drug was essential for the patients' safety reasons.

5. Intervention
   a. "Usual" Therapy
   All procedures and drugs normally given for infants undergoing cardiopulmonary bypass were given routinely. A list of medications provided is shown in FIG. 7B.
   b. "Intervention" Therapy
   The intervention involved DCA (50 mg/kg) or placebo injected into the aortic root immediately prior to removing aortic cross clamp. The coded solution was made such that a dose of 1 ml/kg provides the appropriate dose of DCA or placebo. Based on the pharmacokinetics of DCA, this was expected to result in plasma levels of DCA in the therapeutic range of (1 mM). All blood samples were analyzed by HPLC for DCA concentration.

6. Sample Collections
   Arterial blood samples were obtained from patients at the following times:
   a. Immediately after the insertion of arterial line in operating room, i.e., the beginning of surgery.
   b. Thirty minutes after the bolus of DCA was given, whether or not cardiopulmonary bypass had been discontinued.
   c. One hour after discontinuing cardiopulmonary bypass.
   d. Six hours after discontinuing cardiopulmonary bypass.
   e. Twelve hours after discontinuing cardiopulmonary bypass.
   f. Twenty four hours after discontinuing cardiopulmonary bypass.

7. Sample Processing
   Blood samples were collected from indwelling arterial lines into citrate-containing tubes (0.5 ml blood samples). The samples were spun in the microfuge, the plasma separated, and frozen immediately for later analysis. All plasma samples were stored at −80 degrees centigrade, until further processing. Plasma glucose and lactate were determined using a Sigma glucose kit and a spectrophotometric assay involving lactate dehydrogenase respectively. Plasma fatty acid levels were measured using an ELISA system and WAKO free fatty acid kit.

8. Inotrope Drug Score
   In both the operating room at the end of cardiopulmonary bypass and in the intensive care unit, parenteral drugs were scored on an hourly basis with 1 point allotted for each level for each bolus or infusion given within the previous hour for the first 24 hours post-operatively. Thus, at the end of 24 hours high scores indicated poorer cardiac function.

9. Validation of Index
   In this study, we anticipated a 30% decrease in Inotrope Score at the 1 hour interval.

10. Ascertainment of Response Variables
    a. Data Collection
    The drug score chart in the operating room was filled out by the anesthetist. In the pediatric intensive care unit, the research coordinator was responsible for completing drug score charts, corroborated by nursing staff, ICU staff and physicians. Fatty acids, glucose, DCA, and lactate levels were determined with technicians blinded as to treatment category.
    b. Data Monitoring and Safety issues
    Careful attention was paid to safety precautions in this study. A data monitoring committee had the authority to terminate the study should have serious adverse side effects occurred. In previous pilot studies, no adverse effects of DCA were noted.
    c. Data Analysis
    DCA was deemed beneficial if Inotrope Score was significantly lower in the intervention patients than in placebo patients.

11. Statistical Analysis
    Comparison of demographics between groups was done using unpaired t-tests (continuous variables) and Chi-square tests (discrete variables). Comparison of Cardiac functional Index between groups was done using a nonparametric unpaired test. Statistical significance is defined as $p<0.05$. Data handling and statistical analysis was performed by the Epicore Center.

Results of Study

Figure 4:
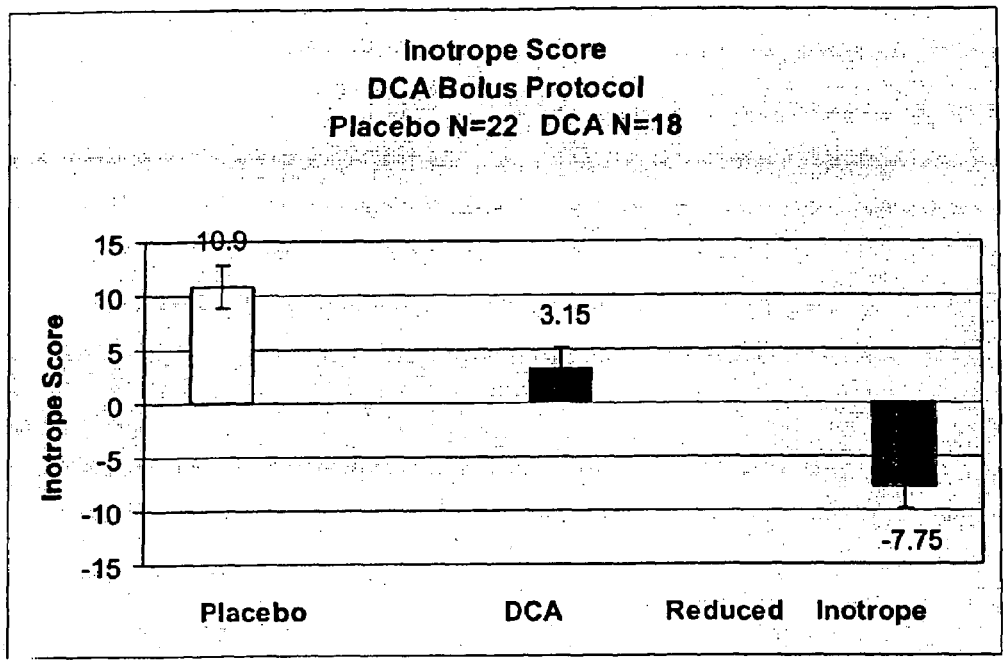
FIG. 4 depicts a graph for the inotrope score for patients treated with DCA (50 mg/kg bolus) versus placebo and the relative decrease in 1 hour inotrope score of DCA treated patients compared to placebo. See Example B.

DCA administration significantly reduced the need for inotropic drugs during the critical first 1 hour period following surgery (FIG. 4). Data from this bolus administration of DCA to pediatric patients (40) also demonstrates that post surgical DCA administration reduces ICU time (FIG. 5) and ventilator time (FIG. 6). In this protocol which had 40 pediatric patients, 18 pediatric patients received a DCA bolus of 50 mg/kg. Echocardiography in the DCA patients (35% versus 26%) demonstrated better shortening fraction as compared to placebo patients.

Example C

Description of Study Protocol

This study was a randomized, placebo-controlled, double blinded, single surgeon, study of the use of DCA in 51 high-risk pediatric patients requiring heart surgery to correct complex congenital heart lesions.

1. Study Population
   In this trial, 53 infants were recruited to participate in a study, of which 51 patients met inclusion criteria after parental consent. Two dosing groups resulted from the study team changing the dosing protocol after the data from the initial 10 patients were analyzed. The data from patients number 1 to number 10 was analyzed for DCA therapeutic blood levels and therapeutic effect. A recommendation by the research team was made to increase the bolus dose of DCA and to decrease the infusion dose of DCA to maintain a DCA dose range of 1 mM for 24 hours. The intent was to administer the new protocol at patient number 20. The 1997 Epicore power calculations were based on separation of the study groups patients into group A of n=20 patients and Group B of n=31 patients
   Half of each group received different dosages of DCA and the other half received placebo in a double blinded, randomized fashion. Candidates for entry into the study were recruited from weekly surgical lists and from notification by the cardiac surgeon.

2. Inclusion criteria
   a) Age less than 1 year.
   b) Consent from parent or guardian.
   c) Requirement for open-heart surgery to correct complex congenital heart lesions (e.g., tetralogy of Fallot).
   d) Agreement of the surgeon, anesthetist, and cardiologist.

3. Exclusion Criteria
   a) Lack of parental consent.
   b) Refusal for entry from surgeon or anesthetist or cardiologist.
   c) Significant non cardiac complications precluding study protocol implementation.

4. Randomization, Data Collection, and Blinding Procedures
   Computerized randomization of study medications were performed by the Epicore Centre. The patients and all study personnel were blinded throughout the study. Unblinding was set into the procedures only if, in the opinion of the patient's physician or study personnel, information concerning the identity of the study drug was essential for the patients' safety reasons.

5. Intervention
   a) "Usual" therapy
   All procedures and drugs normally given for infants undergoing cardiopulmonary bypass were given routinely. A list of medications provided in shown in FIGS. 7A and 7B.
   b) "Intervention" therapy
   The interventions in the two groups of this study were as follows:
   (i) Group A
   DCA (50 mg/kg) or placebo was injected into the aortic root immediately prior to removing aortic cross clamp. The coded solutions were made such that a dose of 1 ml/kg provided either a DCA therapeutic level of 1 mM plasma concentration of DCA, or a placebo solution. Immediately thereafter, an infusion of DCA at 25 mg/kg/hr or placebo in the same volume was initiated and run for 24 hours. Based on the pharmacokinetics of DCA, this was expected to maintain plasma levels of DCA in the therapeutic range of (0.2-1 mM). However, the plasma concentrations of DCA were below 1 mM after the first hour interval, and that the 24 hour plasma concentrations were elevated above 1 mM DCA levels at the 24 hour interval, a decision was made to modify the dosing protocol. This change in dosing protocol was approved by the Ethics Committee, but not implemented until patient number 24. All blood samples were analyzed by HPLC for DCA concentration.
   (ii) Group B
   DCA (100 mg/kg) or placebo was injected into the aortic root immediately prior to removing aortic cross clamp. The coded solutions were made such that a dose of 1 ml/kg provided either a DCA therapeutic level of 1 mM plasma concentration of DCA, or a placebo solution. Immediately thereafter, an infusion of DCA at 12.5 mg/kg/hr or placebo in the same volume was initiated and run for 24 hours. Based on the pharmacokinetics of DCA, this was expected to maintain plasma levels of DCA in the therapeutic range of (0.2-1 mM). All blood samples were analyzed by HPLC for DCA concentration.

6. Sample collections
   Arterial blood samples were obtained from patients at the following times:
   a. Immediately after the insertion of arterial line in operating room (i.e., at beginning of surgery).
   b. Thirty minutes after the bolus of DCA has been given, whether or not cardiopulmonary bypass has been discontinued.
   c. One hour after discontinuing cardiopulmonary bypass.
   d. Six hours after discontinuing cardiopulmonary bypass
   e. Twelve hours after discontinuing cardiopulmonary bypass.
   f. Twenty four hours after discontinuing cardiopulmonary bypass.
   At the end of 24 hours, the DCA or placebo infusion was discontinued.

7. Sample processing
   Blood samples were collected from indwelling arterial lines into citrate-containing tubes (0.5 ml blood samples). The samples were spun in the microfuge, the plasma separated, and frozen immediately for later analysis. All plasma samples were stored at −80 degrees centigrade, until further processing. Plasma glucose and lactate were determined using a Sigma glucose kit and a spectrophotometric assay involving lactate dehydrogenase respectively. Plasma fatty acid levels were measured using an ELISA system and WAKO free fatty acid kit.

8. Inotrope Drug Score
   In both the operating room at the end of cardiopulmonary bypass and in the intensive care unit, parenteral drugs were scored on an hourly basis with 1 point allotted for each level for each bolus or infusion given within the previous hour within the first 24 hours post-operatively. Thus at the end of 24 hours, high scores indicated poorer cardiac function.

9. Validation of Index
   In this study, we anticipated a 30% decrease in Inotrope Score. Our intent was to maintain good or improve contractile function through the 24 hour period as compared to placebo, by providing an infusion of DCA throughout the 24 hour period following a bolus administration of DCA. By improving cardiac function, we anticipated a reduction in ICU time per patient.

10. Ascertainment of Response Variables
    a) Data collection
    The drug score charts in the operating room were filled out by the anesthetist. In the pediatric intensive care unit, the research coordinator was responsible for completing drug score charts, corroborated by nursing, ICU flow sheets, and doctor's orders. Fatty acids, glucose, DCA, and lactate levels were determined with technicians blinded as to treatment category.
    b) Data monitoring and safety issues
    Careful attention was paid to safety precautions in this study. A data monitoring committee has the authority to terminate the study should have serious adverse side effects occurred. In previous studies, no adverse effects of DCA were noted.
    c) Data Analysis
    DCA was deemed beneficial if Inotrope Score was significantly lower in the Intervention patient compared to the placebo patients.

11. Statistical Analysis
    Comparison of demographics between groups was done using unpaired t-tests (continuous variables) and Chi-square tests (discrete variables). Comparison of Cardiac functional Index between groups was done using a nonparametric unpaired test. Statistical significance is defined as $p<0.05$.

Data Handling and statistical analysis was performed by the Epicore Center.

Results of Study

Since DCA has a short-half life in the body this study was initiated in pediatric patients where a DCA bolus and infusion protocol was used over a 24 hour period in the presence of other clinically recommended doses of hemodynamic drugs (FIGS. 7A and 7B). The goal of this study was to maintain therapeutic levels of DCA over a 24 hour period because it is known that poor myocardial contractility and high lactate levels (10) persist for up to 24 hours in children after open heart surgery.

In a double-blinded randomized clinical trial involving 51 pediatric patients (age 3 days to 12 years) requiring open-heart surgery were given either a DCA bolus or placebo followed by an infusion of DCA for 24 hours. During the course of this study, after the protocol was administered to first 10 patients in the Group A (out of the 24 patients), it became clear that the original Group A infusion rate produced concentrations of DCA in excess of 1 mM by 24 hours. We therefore modified the Group A bolus infusion protocol, as described in the "Methods" section for Group B in this document. In the Group A, 12 patients received a DCA bolus of 50 mg/kg followed by an infusion of DCA (25 mg/kg/hr) for 24 hours. In the Group B, 14 patients received a DCA bolus of 100 mg/kg followed by an infusion of DCA (12.5 mg/kg/hr) for 24 hours.

The following observations were as follows from this study: There was also a trend toward lower Inotrope Scores in the DCA groups over the 24 hour period as compared to placebo. There was also a trend toward less Intensive Care Unit (ICU) days in the DCA groups over the 24 hour period as compared to placebo. There was also a trend toward less ventilator time in DCA Group A as compared to placebo. This decrease in ventilator time was lower than what was observed from both the DCA Group B protocol and the DCA protocol of the Study described in Example B. Greater differences in ICU Time were observed in patients who had poorer initial function with more complex conditions and surgical procedures, which suggests that DCA may be more beneficial then placebo for these patients.

A subsequent review of the data obtained from the 51 patients in this study revealed the following. The change in dosing protocol in this study was initiated at patient number 25 (and not at patient number 20 as anticipated at the time of request for protocol change), and that the actual number of patients allocated to each group was 24 patients for the Group A, and 27 patients for the Group B. Subsequent review of the patient records and data of the 24 older, pediatric patients in the Group A revealed the inclusion of 1 infusion pump failure case. In the 27 younger, pediatric patients in the Group B, there were 3 infusion pump failure cases. In total, 4 only infusion pump failure cases were excluded in the subsequent data compilation. As a result of the infusion pump failure modifications, the final allocation of patients included in the final two groups in this document were as follows: Group A of n=23 patients and Group B of n=24 patients. The drug scoring compilation of data was set up for Inotrope Scoring, and not Na+CO3 scores. (Na+C03 is not currently a routinely used hemodynamic drug in recommended protocols for surgical heart procedures.) As a result, Na+C03 scores were removed in the final compilation of the Inotrope Scoring data. Clinically recommended doses of other hemodynamic drugs administered to both the placebo and drug patient groups were noted (see FIGS. 7A and 7B).

1. Inotrope Score

In this study, a trend in decreased Inotrope Score over the 24 hour period post-surgery was shown, similar to what was observed in the study described in Example B (FIG. 4) over the 1 to 4 hour period. A trend to a decreased inotrope use was noted in both Group A, and Group B patients receiving DCA. Data from the study, Group A (FIG. 8) and Group B (FIG. 9), show the effects of DCA bolus/infusion administration using the two dosing protocols on Inotrope Score over the 24 hour period. In the Group B (FIG. 9), the decrease in Inotrope Score (an average decrease of 51% per patient as compared to placebo) was greater than the results from the Group A (an average decrease of 44% per patient as compared to placebo). It should be noted that in this study, all patients in the A and B Groups on average received lower Inotrope Scores than those reported for the patients in the study described in Example B patients, due to the involvement of a different cardiac surgeon.

2. ICU Time

Figure 5:
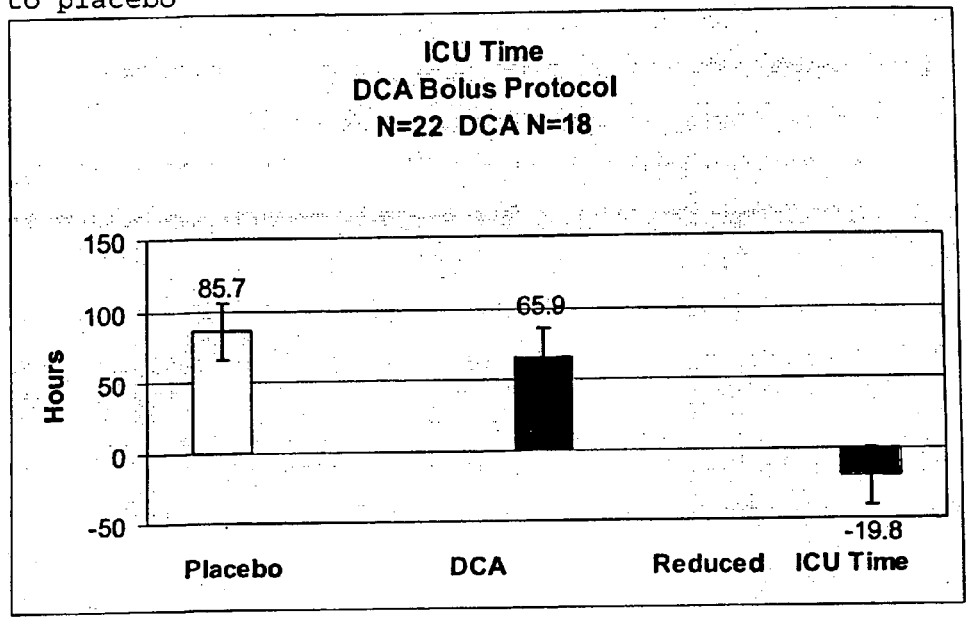
FIG. 5 depicts a graph of decrease in ICU time for patients treated with DCA (50 mg/kg bolus) as compared to placebo. See Example B.
Figure 6:
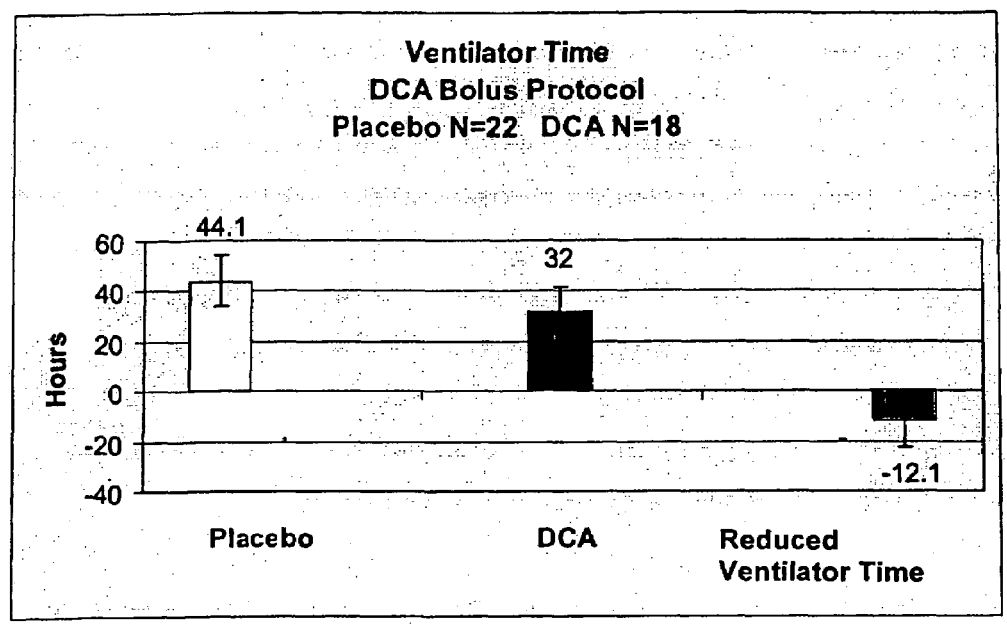
FIG. 6 depicts a graph of the decrease in ventilator time for patients treated with DCA (50 mg/kg bolus) versus placebo. See Example B.

In this study Group A, and Group B, a trend in decreased ICU time was similar to what was observed in the study described in Example B (FIG. 5). A trend to decreased ICU time over the 24 hour period was noted in both Group A and Group B patients receiving DCA. Data from the Group A (FIG. 10) and Group B (FIG. 11), show the effects of DCA bolus/infusion administration on ICU time, using the two different dosing protocols. In Group A, the reduction in ICU time (a decrease of 60 hours or 41% as compared to placebo), was greater than the results from both the study described in Example B (a decrease of 19 hours or 23% compared to placebo), and the Group B (a decrease of 50 hours, or 40% compared to placebo).

3. Ventilator Time

Data from the Group A and Group B showed that the trend in decreased ventilator time was similar to what was observed in the study described in Example B (FIG. 6). A trend to decreased ventilator time over the 24 hour period was noted in both Group A and Group B patients receiving DCA. Data from the Group A (FIG. 12) and Group B (FIG. 13) show the effects of DCA bolus/infusion administration on ventilator time using the two different dosing protocols. In Group A, the reduction in ventilator time (a decrease of 46 hours or 47% as compared to placebo) was greater than the results from both the study described in Example B (a decrease of 12 hours or 27% compared to placebo) and the Group B (a decrease of 18 hours or 23% compared to placebo).

Conclusion

In summary, our findings support our first outcome measure to improve cardiac function through a measurement score "cardiac index" which showed a reduced need for inotropes, and a reduced ICU time and reduced ventilator time post-surgery as compared to placebo. We have established through our three studies that DCA improves cardiac function and provides cardioprotection during reperfusion in both neonates and adults as additive and/or in combination therapy with hemodynamic drugs. The data from these studies supports the use of DCA as a therapeutic approach for treating both the adult and pediatric cardiac surgical patients. The data also supports the combined used of DCA with inotropes in the presence of other clinically recommended doses of hemodynamic drugs, and demonstrates that DCA can lessen the amount of inotropes needed post-surgery.

References:

1. Bersin R M, Wolfe C, Kwasman M, Lau D, Klinski C, Tanaka K, Khorrami P. Henderson G N, D E Marco T, Chatterjee K: Improved hemodynamic function and mechanical efficiency in congestive heart failure with sodium dichloroacetate. JACC 1994;23(7): 1617-1624.

2. Chandler B M, Sonnenblick E H,. Pool F E: Mechanochemistry of cardiac muscle III. Effects of norepinephrine on the utilization of high energy phosphates. Circ Res 1968; 22:729-735.

3. Suga H, Hisano R, Goto Y, Yamada 0, Igarashi Y: Effect of positive inotropic agents on the relation between oxygen consumption and systolic pressure volume area in canine left ventricle. Circ Res 1983;53:306-318.

4. Hasenfuss G, Mulieri L A, Allen P D, Just H, Alpert N R: Influence of isoproterenol and ouabain on excitation-contraction coupling, crossbridge function and energetics in failing human myocardium. Circulation 1996;94:3 155-3160.

5. Lopaschuk G D: Alterations in fatty acid oxidation during reperfusion of the heart after myocardial ischemia. Am J Cardiol 1997;80(3A): 1 1A-16A.

6. Stanley W C, Lopaschuk G D, Hall J L, McCormack J G: Regulation of myocardial carbohydrate metabolism under normal and ischemic conditions potential for pharmacological interventions Cardiovascular Res 1997,33 243-257

7. Lopaschuk G D, Saddik M: The relative contribution of glucose and fatty acids to ATP production in hearts reperfused following ischemia. Mol Cell Biochem 1992;116:1 11-116.

8. Collins-Nakai R L, Noseworthy D, Lopaschuk G D: Epinephrine increases ATP production in hearts by preferentially increasing glucose metabolism. Am J Physiol 1994; 267:H1862-H1871.

9. Lopaschuk G D, Wambolt R B, Barr R L: An imbalance between glycolysis and glucose oxidation is a possible explanation for the detrimental effects of high levels of fatty acids during aerobic reperfusion of ischemic hearts. J Pharmacol Exp Ther 1993;264: 135-144.

10. Lopaschuk G D, Collins-Nakai R, Olley P M, Montague T J, McNeil G, Gayle M, Penkoske P, Finegan B A: Plasma fatty acid levels in infants and adults after myocardial ischemia. Am Heart J 1994; 128:61-67

11. Vik-Mo H, Mjos O D: Influence of free fatty acids on myocardial oxygen consumption and ischemic injury. Am J Cardiol 198 1;48:361-364.

12. Lopaschuk G D: Treating ischemic heart disease by pharmacologically improving cardiac energy metabolism. Am J Cardiol 1998;82: 14K-17K.

13. Itoi T, Lopaschuk G D: The contribution of glycolysis, glucose oxidation, lactate oxidation; and fatty acid oxidation to ATP production in isolated biventricular working hearts from 2-week old rabbits. Ped Res 1993;34(6):735-741.

14. Stacpoole P W, Henderson G N, Yan. Z, Cornett R, James M O: Pharmacokinetics, metabolism and toxicology of dichloroacetate. Drug Met Rev 1998;30(3):499-538.

15. Saddik M, Gamble J, Witters L A, Lopaschuk G D: Acetyl-CoA carboxylase regulation of fatty acid oxidation in the heart. J Biol Chem 1993;268(34):25836-25845.

16. Lui B, Clanachan A S, Schulz R, Lopaschuk G D: Cardiac efficiency is improved after ischemia by altering both the source and fate of protons. Circ Res 1996;79:940-948.

17. McVeigh J J, Lopaschuk G D: Dichloroacetate stimulation of glucose oxidation improves recovery of ischemic rat hearts Am J Physiol 1990,259 H1079-H1085

18. Bersin R M, Stacpoole P W: Dichloroacetate as metabolic therapy for myocardial ischemia and failure. Am Heart J 1997; 134:841-855.

19. Lopaschuk G D, Collins-Nakai R L, Itoi T: Developmental changes in energy substrate use by the heart. Cardiovasc Res 1992;26: 1172-1180.

20. Makinde A, Kantor P F, Lopaschuk G D: Maturation of fatty acid and carbohydrate metabolism in the newborn heart. Mol Cell Biochem 1998; 188:49-56.

21. Itoi T, Huang L, Lopaschuk G D: Glucose use in neonatal rabbit hearts reperfused after global ischemia. Am J Physiol 1993;265: H427-H433.

22. Lopaschuk G D, Spafford M A: Energy substrate utilization by isolated working hearts from newborn rabbits. Am J Physiol 1990;258: H1274-H1280.

23. Saiki Y, Lopaschuk G D, Dodge K, Yamaya K, Morgan C, Rebeyka TM: Pyruvate augments mechanical function via activation of the pyruvate dehydrogenase complex in reperfused ischemic immature rabbit hearts. J Surg Res 1998;79: 164-169.

We claim:

1. A pharmaceutical composition comprising a cardioprotective amount of dichloroacetate (DCA) sufficient to maintain a plasma DCA level of at least about 1 mM for at least about 1 hour, and an inotrope selected from the group consisting of dobutamine, epinephrine, dopamine, norepinephrine, phenylephrine, phentolamine, digoxin, amrinone and milrinone, wherein the inotrope is present at a therapeutically effective concentration that provides a lower dose than the dose of inotrope that would be therapeutically effective in the absence of DCA.

2. A pharmaceutical composition according to claim 1 in a formulation suitable for administration by continuous infusion.

3. A pharmaceutical composition according to claim 1 in a formulation suitable for administration of a bolus of DCA followed by continous infusion of DCA, wherein said plasma DCA level is maintained by continuous infusion after a bolus of at least about 50 mg/kg.

4. A method of maintaining cardiac function in a patient during and following an ischemic event and during reperfusion thereafter which comprises administering to said patient a cardioprotective amount of dichloroacetate (DCA) sufficient to maintain a plasma DCA level of at least about 1 mM for at least about 1 hour, with a therapeutically effective dose of an inotrope sufficient to maintain said cardiac function, wherein said dose is lower than the dose of inotrope that would be therapeutically effective in the absence of DCA.

5. A method according to claim 4 wherein said ischemic event is a surgical heart procedure.

6. A method according to claim 5 wherein DCA is administered continuously to the patient.

7. A method according to claim 6 wherein said plasma DCA level is maintained for at least about 24 hours.

8. A method according to claim 5 wherein said surgical heart procedure is an open heart surgical procedure.

9. A method according to claim 5 wherein DCA and inotrope are administered during reperfusion and following the procedure.

10. A method according to claim 4 wherein said ischemic event is hemorrhagic shock, hypoxia or trauma.

11. A method according to claim 4 wherein said inotrope is selected from the group consisting of dobutamine, epinephrine, dopamine, norepinephrine, phenylephrine, phentolamine, digoxin, amrinone and milrinone.

12. A method according to claim 4 wherein DCA is administered as a bolus, followed by continuous administration of DCA and inotrope in combination for at least about 24 hours.

13. A method of maintaining cardiac function at a predetermined level in a patient in need of treatment while decreasing the dose of inotrope needed to maintain said cardiac function, which comprises administering to said patient dichloroacetate (DCA) in a bolus of at least about 100 mg/kg, followed by continuous infusion of DCA at a dose of at least about 12.5 mg/kg/hour for at least about one hour.

14. A method according to claim 13 wherein said inotrope is selected from the group consisting of dobutamine, epinephrine, dopamine, norepinephrine, phenylephrine, phentolamine, digoxin, amrinone and milrinone.

15. A method according to claim 13 wherein DCA is administered for at least about 24 hours.

16. A method according to claim 5, further comprising maintaining cardiac function at a predetermined level after cardiac surgery in a patient treated with a hemodynamic drug.

17. A method according to claim 16 wherein DCA is administered following said cardiac surgery.

18. A method according to claim 17 wherein DCA is administered during reperfusion and following the procedure.

19. A method according to claim 16 wherein said patient was treated pre-operatively with said hemodynamic drug.

20. A method according to claim 19 wherein said hemodynamic drug is selected from the group consisting of ACE I (an angiotensin converting enzyme (ACE) Inhibitor), AsA (aspirin) and Coumadin.

21. A method according to claim 20 wherein said hemodynamic drug is administered with or without beta blockers and/or with or without nitroglycerin.

22. A method according to claim 16 wherein said patient is treated post-operatively with said hemodynamic drug.

23. A method according to claim 22 wherein said drug is selected from the group consisting of a nitrate, a vasodilator, a Ca antagonist, a beta-blocker and a diuretic.

24. A method of maintaining cardiac function at a predetermined level in a patient in need of treatment while decreasing the dose of inotrope needed to maintain said cardiac function, which comprises administering to said patient dichloroacetate (DCA) in a bolus of at least 50 mg/kg followed by continuous infusion of DCA at a dose of at least about 12.5 mg/kg/hour for at least about one hour in combination with a therapeutically effective dose of an inotrope sufficient to maintain said cardiac function, wherein said dose is lower than the dose of inotrope that would be therapeutically effective in the absence of DCA.

25. A method according to claim 24 wherein said inotrope is selected from the group consisting of dobutamine, epinephrine, dopamine, norepinephrine, phenylephrine, phentolamine, digoxin, amrinone and milrinone.

26. A method according to claim 25 wherein continuous infusion of DCA is at a dose of at least about 25 mg/kg/hour.

* * * * *